US010500240B2

(12) United States Patent
Kalidindi

(10) Patent No.: US 10,500,240 B2
(45) Date of Patent: Dec. 10, 2019

(54) USE OF TERMINALIA CHEBULA EXTRACT FOR TREATMENT OF OSTEOARTHRITIS

(71) Applicant: Natreon, Inc., New Brunswick, NJ (US)

(72) Inventor: Sanyasi R. Kalidindi, Monroe, NJ (US)

(73) Assignee: Natreon, Inc., New Brunswick, NJ (US)

( * ) Notice: Subject to any disclaimer, the term of this patent is extended or adjusted under 35 U.S.C. 154(b) by 578 days.

(21) Appl. No.: 14/578,793

(22) Filed: Dec. 22, 2014

(65) Prior Publication Data

US 2015/0174184 A1 Jun. 25, 2015

Related U.S. Application Data

(60) Provisional application No. 61/919,065, filed on Dec. 20, 2013.

(51) Int. Cl.
*A61K 36/185* (2006.01)
*A61K 31/7048* (2006.01)

(52) U.S. Cl.
CPC ........ *A61K 36/185* (2013.01); *A61K 31/7048* (2013.01)

(58) Field of Classification Search
None
See application file for complete search history.

(56) References Cited

U.S. PATENT DOCUMENTS

| | | | |
|---|---|---|---|
| 6,517,861 | B2 | 2/2003 | Singh et al. |
| 7,338,674 | B2 | 3/2008 | Palpu et al. |
| 7,618,663 | B2 | 11/2009 | Palpu et al. |
| 2013/0266676 | A1 | 10/2013 | Ghosal et al. |

FOREIGN PATENT DOCUMENTS

| | | | | |
|---|---|---|---|---|
| JP | 405331041 | A | 12/1993 | |
| WO | WO-02085394 | A1 * | 10/2002 | ............. A61K 36/00 |
| WO | WO-2011033524 | A2 * | 3/2011 | ............. A61K 36/60 |
| WO | 2011089615 | | 7/2011 | |

OTHER PUBLICATIONS

Ilaaj Barae Deru. From Qaraabaadeen Najm-al-Hhani (20th century AD), Munshi Nawal Kishore Lucknow, (second edition) 1928 AD, p. 321. Author: Mohammad Najuml Ghani Khan. Retrieved from TKDL. [Retrieved from the Internet on: Apr. 30, 2017].*
McConnell et al. Arthritis Care & Research 45:453-461, 2001. pp. 453-461.*
Ranjini et al. The Bioscan. 10(2): 549-551. (Year: 2015).*
Dhanani et al. Journal of Chromatographic Science. 53:625-632 (Year: 2015).*
A. Bag, et al., "Anti-inflammatory, anti-lipid peroxidative, antioxidant and membrane stabilizing activities of hydroalcoholic extract of Terminalia chebula fruits," Pharm. Biol. Dec. 2013; 26(9):1331-1335 (Abstract Only).
A.M. Bendele, "Animal models of osteoarthritis," J. Musculoskelet. Neuronal Interact. (2001) 1(4):363-376 (Abstract Only).
K.D. Brandt, "Animal models of osteoarthritis," Biorheology (2002) 39:221-235 (Abstract Only).
S.J. Kim, et al., "Effect of 1,2,3,4,6-penta-O-galloyl-beta-D-glucose on elastase and hyaluronidase activities and its type II collagen expression," Acta Pol. Pharm. (2010) 67(2):145-150 (Abstract Only).
C.B. Little and M.M. Smith, "Animal models of osteoarthritis," Current Rheumatology Reviews (2008) 4:1-8.
V. Nair, et al., "Anti-arthritic and disease modifying activity of Terminalia chebula Retz. In experimental models," J. Pharm. Pharmacol. (2010) 62(12):1801-1806 (Abstract Only).
J.B. Seo, et al., "Anti-Arthritic and Analgesic Effect of NDI10218, a Standardized Extract of Terminalia chebula, on Arthritis and Pain Model," Biomol. Ther. (Seoul) (2012) 20(1):104-112.
W.B. Van Den Berg, "Lessons from animal models of osteoarthritis," Current Opinion in Rheumatology (2001) 13 (Abstract Only). (5):452-456.
Arzani, Mohammad Akbar; "Qaraabaadeen Qaadri", (17th century AD), 1968 AD, p. 255-256, Ahmadi Publication, Delhi.
Basavaraja; "Basavaraajiyam", Edn. 1st Reprint, 2005 (Time of Origin 15th Century), p. 85, Chaukhambha Sanskrit Pratisthan, Delhi.
Bin Zakariyya Al Razi, Abu Bakr Mohammad; "Kitaab al-Haawi-fil-Tibb", vol. XI (9th century AD), (First Edition) 1962 AD, p. 151, Daycrah al Ma'aarif Usmania, Hyderabad.
Cakrapanidattah; "Cakradattah", Ed. 4th 2002, p. 160, Chaukhamba Sanskrit Samsthan (Varanasi).
Madhavah; "Vrndamadhava", Edn. 1922 (Time of Origin 9th century), p. 316, Yagyeswara Gopal Dixit, Bookseller, Pune.

(Continued)

*Primary Examiner* — Amy L Clark
(74) *Attorney, Agent, or Firm* — Amin Talati Wasserman LLP; George M. Carrera, Jr.; Brent A. Batzer

(57) ABSTRACT

The present invention provides an optimized and/or enriched hydrolyzable tannoid blend derived from *Terminalia chebula*. In an embodiment the present invention further relates to the use of an extract of *Terminalia chebula* for treatment of osteoarthritis. In another embodiment, a *T. chebula* extract composition contains about 8-25% by weight chebulagic acid, about 15-30% by weight chebulinic acid and about 10-40% by weight other low molecular weight hydrolyzable tannoids. This embodiment provides a *T. chebula* enriched tannoid blend composition (TC/enriched tannoid blend). In another embodiment, a method of treating osteoarthritis in an individual is provided, comprising administering to the individual in need thereof a therapeutically effective amount of the *T. chebula* extract composition. In yet another embodiment, a method of reducing pain and inflammation in an individual afflicted with osteoarthritis is provided, comprising orally administering to the individual in need thereof a therapeutically effective amount of the *T. chebula* extract composition.

13 Claims, No Drawings

(56) References Cited

OTHER PUBLICATIONS

Author Compiled by Naginadasa Chaganalala Saha : Translated by Gopinath Gupta—vol. I Title of publication—Bharata Bhaisajya Ratnakara [This book contains back references from 1000 B.C.to 20th century] Page(s) being submitted—7 (p. 4-10) (Ref. p. of publication:44) Publication Date—Edn. 2nd. Reprint. Aug. 1999 Publisher—B. Jain Publishers Place of Publication—New Delhi, India.†

Author Title of publication—Ayurveda Sarasamgrahah—Page(s) being submitted—6 (p. 11-16) (Ref.p. of publication:523-524) Publication Date—Edn. 2003 Publisher—Shrl Baidyanath Ayurveda Bhavan Limited Place of Publication—Calcutta. India.†

Author Lankapatiravana;—Edited and translation by Indradeva Tripathi; Title of publication—Arkapraksah Page(s) being submitted—8 (p. 17-24)—(Ref.p. of publication:88) Publication Date—Edn. 1st 1995 Publisher—Krishnadas Academy Place of Publication—Varanasi, India.†

\* cited by examiner
† cited by third party

USE OF TERMINALIA CHEBULA EXTRACT FOR TREATMENT OF OSTEOARTHRITIS

This application claims the benefit of earlier filed U.S. Provisional Application No. 61/919,065, filed on Dec. 20, 2013, which is hereby incorporated by reference herein.

FIELD OF THE INVENTION

The present invention relates to an enriched hydrolyzable tannoid blend derived from *Terminalia chebula*. The present invention further relates to the use of an extract of *Terminalia chebula* for treatment of osteoarthritis.

BACKGROUND

Arthritis is a form of joint disorder that involves inflammation of one or more joints. There are over 100 different forms of arthritis. The most common form, osteoarthritis (degenerative joint disease), is a result of trauma to the joint, infection of the joint, or age. Other arthritis forms are rheumatoid arthritis, psoriatic arthritis, and related autoimmune diseases. Septic arthritis is caused by joint infection. The major complaint by individuals who have arthritis is joint pain. Pain is often a constant and may be localized to the joint affected. The pain from arthritis is attributed to multiple factors including inflammation that occurs around the joint, damage to the joint from disease, daily wear and tear of joint, muscle strains caused by forceful movements against stiff painful joints, and fatigue.

Osteoarthritis (OA) is the most common form of arthritis. In mammals, it can affect both the larger and the smaller joints of the body, including the hands, wrists, feet, back, hip, and knee. The disease is essentially one acquired from daily wear and tear of the joint; however, OA can also occur as a result of injury. OA begins in the cartilage and eventually causes the two opposing bones to erode into each other. Initially, the condition starts with minor pain during activities, but as the disease progresses the pain can be continuous and even occur while in a state of rest. The pain can be debilitating and prevent one from doing some activities. OA typically affects the weight-bearing joints, such as the back, spine, and pelvis.

Unlike rheumatoid arthritis, OA is most commonly a disease of the elderly. Disease onset is gradual and usually begins after the age of 40. More than 30% of women have some degree of OA by age 65. One in two people in the U.S. will experience some form of OA in their lifetime. OA is much more common in women than men and it accounts for more than 50% of arthritis cases in the U.S. (nearly 27 million of the 46 million adults).

OA cannot be cured, but one can prevent the condition from worsening. Pain medications are widely required by individuals with osteoarthritis. Such medications include analgesics such as acetaminophen and NSAIDs (non-steroidal anti-inflammatory drugs). These medications have side effects, which may be serious in some patients. As a result, patients often rely upon natural products with the hope that they are safer than allopathic medications.

Among natural products used for relief of OA symptoms, glucosamine and chondroitin have the longest stay in the market, despite doubts about their efficacy. A major OA clinical trial on glucosamine and chondroitin was the Glucosamine/chondroitin Arthritis Intervention Trial (GAIT, ClinicalTrials.gov NCT00032890 Glucosamine/Chondroitin Arthritis Intervention Trial). GAIT was funded by National Institutes of Health to test the effects of chondroitin and glucosamine on OA of the knee. This multicenter, placebo-controlled, double-blind, six-month-long trial found that glucosamine plus chondroitin had no statistically significant effect on symptoms of OA in the overall group of OA patients. However, in the moderate-to-severe pain subgroup, the combination of chondroitin and glucosamine was found to be subjectively more effective (in 25% of the patients) in treating pain than celecoxib or chondroitin and glucosamine taken individually. Due to small sample sizes in the subgroup (roughly 250 people), the researchers concluded that this finding needs further validation. The study also found chondroitin sulfate to have no significant effect in reducing joint swelling, effusion, or both. These results indicate that glucosamine and chondroitin do not effectively relieve OA pain in the overall group of osteoarthritis patients, though it may be an effective treatment for those suffering from moderate-to-severe pain.

In a follow-up study (New England Journal of Medicine (2006) 354 (8): 795-808), 572 patients from the GAIT trial continued the supplementation for 2 years. After 2 years of supplementation with glucosamine and chondroitin sulfate, alone or in combination, there was no benefit in slowing the loss of cartilage, in terms of joint space width, when compared to a placebo. Further, in another 2-year follow-up study, there was no significant pain reduction or improved function when compared to a placebo. In addition, glucosamine and chondrotin are produced from crustacean exoskeletons and cartilage, respectively, which may pose a problem for vegetarians and those who are allergic to crustaceans.

Another product recently introduced in the market for relief from OA is undenatured type 2 collagen, which is obtained from chicken cartilage (Int. J. Med. Sci. (2009) 6(6): 312-321). Again, vegetarians may have a problem with the source of this product.

Thus, there is a need for a safe and efficacious vegetarian product for treatment of OA. A possible candidate is *Terminalia chebula* Retz. (Combritaceae), ("TC"), which has been extensively used in Ayurveda, Unani and Homoeopathic systems of medicine for improvement of different health conditions, e.g., constipation, diarrhoea, ulcers, gastroenteritis, asthma, cough, dyspnea, dyspepsia, hemorrhoids, candidiasis, parasites, malabsorption syndrome, hepatomegaly, vesicular and renal calculi, urinary discharges, tumors, skin diseases, leprosy, intermittent fever, rheumatoid arthritis, gout, neuropathy, paralysis, memory loss, epilepsy, depression, leucorrhea, diabetes, cardiovascular diseases, anorexia, and wounds, among others (B. Das, *Materia Medica of Ayurveda* (New Delhi: B. Jain Publishers, 1991), p. 8; K. R. Kirtikar and B. D. Basu, "*Terminalia chebula*." In: *Indian Medicinal Plants*, ($2^{nd}$ Edn., Allahabad, India: Lolit Mohan Basu Publication, 1935), pp. 1020-23; and P. V. Sharma, *Dravya Guna Vigyana* (Vol. 2, Varanasi: Chaukhamba Bharati Academy, 1995), pp. 753-58). *T. chebula* fruit and its different solvent extractives were reported to exhibit hepatoprotective, cardioprotective, antimutagenic/anticarcinogenic, cytoprotective, radioprotective, antioxidant and adaptogenic, antimicrobial, antifungal, antiviral, antiamoebic, immunomodulatory, antidiabetic, wound healing, antispasmodic, and purgative activities in various animal models (S. S. Tasduq, et al., *Human and Exp. Toxicol.* (2006) 25: 11-18; H. Y. Cheng, et al., *Biol. Pharm. Bull.* (2003) 26:1331-5; S. Kaur, et al., *Mutagen Res.* (1998) 419: 169-79; Suthienkul, et al., *South-East Asian Journal Trop. Med., Public Health* (1993) 24: 751-5; Ahmad, et al., *J. Ethnopharmacol.* (1998) 62: 183-93; and N. K. Rao, et al., *BMC Complement. Altern. Med.* (2006) 6: 127-32).

Several animal studies have been carried out to determine the effects of alcoholic/hydro-alcoholic extracts of *T. chebula* on rheumatoid arthritis. Jong Bae Seo, et. al. (Biomol. Therapeut. (Seoul) (2012) January; 20(1): 104-112) studied the effect of an alcoholic extract of *T. chebula* on collagen-induced arthritis in mice and concluded that *T. chebula* extract can be a therapeutic candidate for treatment of rheumatoid arthritis. Nair, et. al. (J. Pharm. Pharmacol. (2010) December; 62(12):1801-6) studied the effect of an hydro-alcoholic extract of *T. chebula* in rats and concluded that this extract has the potential to be used as a disease-modifying agent in rheumatoid arthritis. Kim, et. al. (Acta Pol. Pharm. (2010) March-April; 67(2):145-50) studied 1,2,3,4,6-penta-O-galloyl-beta-D-glucose (PGG), a bioactive compound derived from a methanolic extract of *T. chebula*, on rabbit articular chondrocytes in vitro and reported that type II collagen expression was induced. Kim, et. al. hypothesized that this compound derived from TC might be beneficial in relieving painful joint conditions.

Although animal models are more suited for studying the effect of drugs in rheumatoid arthritis, animal studies for OA do not necessarily predict the efficacy of a product in human beings. A. M. Bendele (J. Musculoskelet. Neuronal Interact. (2001) June; 1(4):363-76) discussed various animal models for osteoarthritis study and concluded that none of these models have a proven track record of proving efficacy in human disease. W. B. van den Berg (Current Opinion in Rheumatology (2001) 13(5):452-456), working with transgenic murine OA models concluded that treatment with a range of disease-modifying drugs showed some efficacy in a number of OA models, but its predictive value for human OA remains obscure. Christopher B. Little and Margaret M. Smith (*Current Rheumatology Reviews* (2008) 4(3): 1-8) opined that none of the animal models of OA is truly predictive for humans, although valuable for discovery purposes. As per Kenneth D. Brandt (Biorheology (2002) Vol. 39, Number 1-2, pp. 221-235), animal models have proved to be of considerable importance in elucidating mechanisms underlying joint damage in osteoarthritis (OA) and providing proof of concept in the development of pharmacologic and biologic agents that may modify structural damage in the OA joint, but the utility of animal models in predicting the response to an intervention with a drug or biologic agent in humans, however, can be established only after evidence is obtained of a positive effect of the agent in humans.

In addition, not all of the TC extracts available in the market are effective because of the absence of certain bioactives—e.g., chebulinic acid and chebulagic acid due to non-optimized extraction processes.

Thus, it is recommended to study an extract of *Terminalia chebula*, optimized to contain the maximum percentages of chebulinic acid and chebulagic acids in humans before asserting its effectiveness in osteoarthritis in humans. The present invention is based on a human clinical study of an optimized extract of *Terminalia chebula* in patients with moderate osteoarthritis.

If a way could be found to treat or prevent the symptoms associated with osteoarthritis using an extract of *Terminalia chebula* in individuals this would represent a contribution to the medical and nutraceutical arts. Further, if a way could be found to treat or prevent the symptoms associated with osteoarthritis using an aqueous extract of *Terminalia chebula*, for example joint pain, this would represent a valuable contribution to the art.

SUMMARY OF THE INVENTION

One objective of the present invention is to provide a safe, efficacious and vegetarian optimized and/or enriched extract of *Terminalia chebula* (TC) for treatment of arthritis, particularly, osteoarthritis in a mammal, particularly a human or an animal.

It is a further objective of the invention to develop an extraction process for *T. chebula* which is substantially aqueous or completely aqueous to obtain an optimized and/or enriched TC extract.

In another embodiment, a *T. chebula* extract composition contains about 8-25% by weight chebulagic acid, about 15-30% by weight chebulinic acid and about 10-40% by weight other low molecular weight hydrolyzable tannoids. This embodiment provides a *T. chebula* enriched tannoid blend composition (TC/enriched tannoid blend).

In another embodiment, a method of treating osteoarthritis in a mammal is provided, comprising administering to the mammal in need thereof a therapeutically effective amount of a *Terminalia chebula* extract composition comprising a hydrolyzable tannoid blend including about 8-25% by weight chebulagic acid based on the total weight of the extract, and about 15-30% by weight chebulinic acid based on the total weight of the extract, and optionally an acceptable carrier. The *Terminalia chebula* extract composition can be administered in a daily dosage from about 100 mg per day to about 5000 mg per day.

In yet another embodiment, a method of reducing pain and inflammation in an individual afflicted with osteoarthritis is provided, comprising orally administering to the individual in need thereof a therapeutically effective amount of a *Terminalia chebula* extract composition comprising a hydrolyzable tannoid blend including about 8-25% by weight chebulagic acid based on the total weight of the extract, and about 15-30% by weight chebulinic acid based on the total weight of the extract, and optionally an acceptable carrier. The *Terminalia chebula* extract composition can be administered in a daily dosage from about 100 mg per day to about 5000 mg per day.

DETAILED DESCRIPTION

*Terminalia chebula* (*T. chebula*) is rich in tannoid principles. The chief constituent tannoids in the fruit are chebulinic acid, chebulagic acid, corilagin and a tannoid metabolite, gallic acid (J. Bruneton. *Pharmacognosy, Phytochemistry, Medicinal Plants*. (Paris, France: Laviosier Publishing, 1995), p. 333). Other minor hydrolyzable tannoids reported in *T. chebula* include punicalagin, chebulanin, neochebulinic acid, 1,2,3,4,6-penta-O-galloyl-β-D-glucose, 1,6,-di-O-galloyl-D-glucose, casuarinin, 3,4,6-tri-O-galloyl-D-glucose, and terchebulin (L. J. Juang, et al., *J. Sep. Sci.* (2004) 27: 718-24). One source lists *T. chebula* as having a tannoids content of about 32% by weight (W. Evans. *Trease and Evan's Pharmacology*. (14th Ed., W.B. Saunders Co. Pvt. Ltd., 1996), p. 493). Other constituents reported in *T. chebula* include fructose, amino acids, succinic acid, beta-sitosterol, resin and purgative principles of anthroquinone, sennoside, flavonol glycosides, triterpenoids and coumarin conjugated with gallic acids (E. Creencia, et al., *KIMIKA* (1996) 12: 1-10).

Chemical constituents isolated from *T. chebula* may vary considerably in type and/or concentration due to a number of factors, e.g., ecological variation, soil variation, and nutrient variation, as well as variations in the process of extraction.

It is thus desirable to provide a potent and therapeutically effective extract of *T. chebula* in a pharmaceutical or nutraceutical composition having improved properties for the treatment or prevention of osteoarthritis (OA).

In an embodiment, a *Terminalia chebula* extract containing a hydrolyzable tannoid blend is provided.

Studies cited above used extracts of *T. chebula* whole fruit. However, *T. chebula* contains several bioactive components, including chebulagic acid, chebulinic acid, chebulic acid and other low molecular weight hydrolyzable tannoids (LMwHTs). Many studies, some of which are described below, have also been done on the individual bioactives of *T. chebula*.

Tannins may be divided into two groups: (a) hydrolyzable tannoids (HTs), which are esters of a polyol or sugar, usually glucose, with one or more trihydroxybenzenecarboxylic acids (i.e., gallates), and (b) derivatives of procyanidins, flavanols or flavanones, so-called condensed tannins HTs are molecules with a polyol (polyfunctional alcohols, generally D-glucose or its derivatives and phenols, namely galloyl and ellagoyl moieties) as a central core. The hydroxyl groups of these carbohydrates are partially or totally esterified with phenolic carboxylic acids like gallic acid (gallotannins), ellagic acid (ellagitannins) or both (gallo-ellagitannins).

Chebulagic acid, depicted in the compound of formula (1), is a tannoid (low Mw polyphenolic) member of the tannin family and has been found as a constituent in many medicinal plants. Chebulagic acid is chemically named as beta-1-O-galloyl-2,4-chebuloyl-3,6-(R)-hexahydroxydiphenoyl-D-glucose.

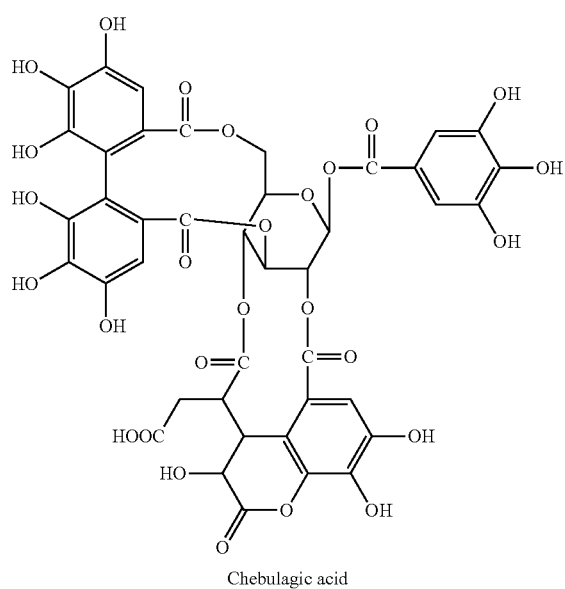

Chebulagic acid

Hydrolyzable tannoids have been reported as key bioactive components of *T. chebula*. Chebulagic acid and chebulinic acid are the two major bioactive hydrolyzable tannoids of *T. chebula*. Chebulagic acid ("CA"), a natural antioxidant, has shown potent anti-inflammatory effects in LPS-stimulated RAW 264.7, a mouse macrophage cell line. These effects were exerted via inhibition of NO and $PGE_2$ production and down-regulation of iNOS, COX-2, 5-LOX, TNF-α and IL-6. CA inhibited NF-κB activation by LPS, and this was associated with the abrogation of IκB-α phosphorylation and subsequent decreases in nuclear p50 and p65 protein levels (D. B. Reddy, et al., *Biochemical and Biophysical Research Communications*. (2009) 381: 112-117).

Chebulagic acid has shown potent COX-LOX dual inhibition activity with $IC_{50}$ values of 15±0.288, 0.92±0.011 and 2.1±0.057 μM for COX-1, COX-2 and 5-LOX, respectively. CA also exhibited anti-proliferative activity against HCT-15, COLO-205, MDA-MB-231, DU-145 and K562 cell lines. Further mechanistic studies on COLO-205 cells revealed induction of apoptosis by chebulagic acid (D. B. Reddy, et al., *J Ethnopharmacol*. (2009) 124: 506-12).

Chebulagic acid, isolated from *Terminalia chebula* Retz, proved to be a reversible and non-competitive inhibitor of maltase with a K(i) value of 6.6 μM. The inhibitory influence of chebulagic acid on the maltase-glucoamylase complex was more potent than on the sucrase-isomaltase complex. The magnitude of alpha-glucosidase inhibition by chebulagic acid was greatly affected by its origin. These results show a use for chebulagic acid in managing type-2 diabetes (Y. N. Huang et al., *Biosci. Biotechnol. Biochem*. (2008) 72: 601-3).

Chebulagic acid has also been shown to synergize the cytotoxicity of doxorubicin in human hepatocellular carcinoma through COX-2 dependent modulation of MDR-1. Chebulagic acid increased the accumulation of doxorubicin in a concentration dependant manner and also enhanced the cytotoxicity of doxorubicin in HepG2 cells by 20 fold. Quantitation of interaction by calculating Combination Index (CI) showed a strong synergistic interaction between chebulagic acid and doxorubicin in terms of cell growth inhibition (C. Achari, et al., *Med Chem*. (2011) 7: 432-42).

Herpes simplex virus 1 (HSV-1) is a common human pathogen that causes lifelong latent infection of sensory neurons. Non-nucleoside inhibitors that can limit HSV-1 recurrence are particularly useful in treating immunocompromised individuals or cases of emerging acyclovir-resistant strains of herpes virus. Chebulagic acid and punicalagin, two hydrolyzable tannoids isolated from the dried fruits of *Terminalia chebula* Retz. (Combretaceae), have been found to inhibit HSV-1 entry at noncytotoxic doses in A549 human lung cells by blocking the interactions between cell surface glycosaminoglycans and HSV-1 glycoproteins (L. T. Lin, et al., *J. Virol*. (2011) 85: 4386-98).

Chebulagic acid has been reported to suppress the onset and progression of collagen-induced arthritis in mice through immune suppression (anticollagen IgG, IL-10, IL-6) via the induction of TGFbeta and CD4+, CD25+ T cells (P. M. Lee, S. I. Hyun, et al., *Arthritis Rheum*. (2005) 52: 345-53).

Chebulagic acid has been reported to possess cytotoxic properties against PRMI-7951 melanoma cells (Y. Kashiwada, et al., *J. Nat. Prod*. (1992) 55: 1033-43).

Chebulinic acid, depicted in the compound of formula (2), is another tannoid member of the tannin family derived from galloyl glucose. Chebulinic acid is chemically named as 1,3,6-tri-O-galloyl-2,4-chebuloyl-beta-D-glucose.

(2)

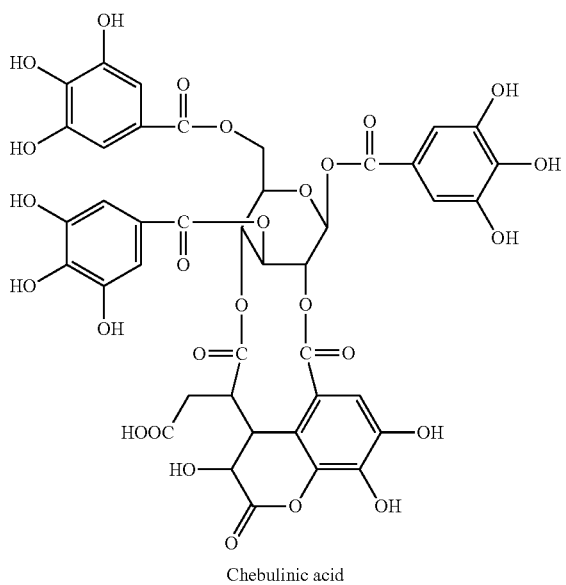

Chebulinic acid

Chebulinic acid and Tellimagrandin I have been shown to exert anti-tumor properties in human cervical carcinoma HeLa cells (Z. C. Yi, et al., *Cancer Lett*. (2006) 242: 77-87).

Chebulinic acid inhibited the hemoglobin synthesis of butyric acid and hemin-treated K562 cells in a concentration-dependent manner. Chebulinic acid has also been reported to inhibit the erythroid differentiation likely through changing transcriptional activation of differentiation relative genes (Z. C. Yi, et al., *Acta Pharmacol Sin*. (2004) 25: 231-8).

Chebulinic acid, tannic acid and ellagic acid were reported to be the growth inhibitory phenolics of *T. chebula* fruits against malignant cell lines including a human (MCF-7) and mouse (S115) breast cancer cell line, a human osteosarcoma cell line (HOS-1), a human prostate cancer cell line (PC-3) and a non-tumorigenic, immortalized human prostate cell line (PNT1A) (A. Saleem, et al., *J Ethnopharmacol*. (2002) 81: 327-36).

Chebulinic acid has been shown to elicit blood pressure lowering effect in rats, likely mediated via the decrease in cardiac output resulting from reduced left ventricular contraction (Y. Y. Guan, et al., *Clin Exp Pharmacol Physiol*. (1996) 23: 747-50).

Chebulinic acid and punicalin were able to block the binding of HIV rgp120 to CD4. These compounds were not toxic to stimulated human peripheral blood lymphocytes at concentrations ten times above their maximal effective concentration (J. L. Weaver, et al., *Biochem. Pharmacol*. (1992) 43: 2479-80).

Gallic acid (GA) and chebulic acid (CA) were isolated from the extract of the herbal medicine Kashi (myrobalan, the fruit of *T. chebula*) as active principle that blocked the cytotoxic T-lymphocyte (CTL)-mediated cytotoxicity. Granule exocytosis in response to anti-CD3 stimulation was also blocked by GA and CA at the equivalent concentrations (S-I. Hamada, et al., *Biological & Pharmaceutical Bulletin*. (1997) 20: 1017-1019).

Chebulagic acid and chebulinic acid have been shown to possess antifibrotic activity through the inhibition of the Smad pathway (H. Y. Chuang, et al., *J. Sci. Food Agric*. (2011) 91:2777-84). Chebulagic acid, chebulinic acid, and other phenolics isolated from *T. chebula*, showed stronger DPPH radical scavenging and melanin inhibitory activities than ascorbic acid, butylated hydroxyl toluene, alpha-tocopherol, arbutin and kojic acid (A. Manosroi, et al., *Nat. Prod. Res*. (2010) 24: 1915-26).

As evidenced by the extensive and significant pharmacological activity of the bioactive constituents and/or components of *T. chebula*, there is a need for these bioactives to be obtained at high levels, up to the maximum possible extent in an extract of this plant. In one embodiment, the present invention contemplates a *T. chebula* extract including an enriched hydrolyzable tannoid blend. The enriched hydrolyzable tannoid blend can include bioactive hydrolyzable tannoids selected from chebulagic acid, chebulinic acid, other low molecular weight hydrolyzable tannoids, and combinations thereof.

HPLC Analytical Method

The active constituents include a combination of chebulagic acid, chebulinic acid, and other Low Molecular weight Hydrolysable Tannoids (LMwHTs).

Sample Preparation. 50 mg of *T. chebula* powdered extract (aqueous extract) is dispersed in 10 ml of double distilled water. The dispersion is sonicated for 10 minutes and then centrifuged at 8500 rpm for 10 minutes. The resulting supernatant at a concentration of 5 mg/ml is injected (20 μl) for a typical HPLC run cycle.

HPLC Conditions.

Column: reversed phase C18 LiChroCART, 250 mm 1.×4 mm i.d., 5 μm particle diameter. (E. Merck, Germany).

Column temp.: ambient.

Eluant: aqueous phase [A]: 0.1% formic acid; organic phase [B] acetonitrile (ACN).

Flow rate: 0.8 ml/min.

Run Time: 46 min. Gradient: B 0-15% (1 min), 15-25% (35 min), 25-60% (9 min) and re-equilibriation 60-0% (1 min).

UV detection at 270 nm; Waters HPLC Model 515 with PDA detector (Waters™ 2996, Photodiode Array Detector), evaluation with Empower.

HPLC Evaluation Method. The method was developed with external standards and evaluation of area of peaks using respective calibration equation.

A. Preparation of Linear Regression Equation of Chebulinic Acid.

A reference standard of chebulinic acid (98% w/w pure, isolated from *T. chebula* fruits using Sephadex G-50 (Amersham Bioscience) and Low Pressure Chromatography (Bio-Rad)) was dissolved in distilled water to prepare three different concentrations (40 μg/20 μl, 20 μg/20 μl and 10 μg/20 μl) required for preparation of calibration curve. The prepared concentrations were subjected to HPLC analysis. The peak areas were calculated for each dilution, and the respective concentration was plotted against the peak area. The amount of chebulinic acid, chebulagic acid, chebulinic acid equivalents and chebulagic acid equivalents were determined using regression equation of the calibration curve obtained as follows Y=209490383x+3958610 with a correlation coefficient of 1.0. Y is the peak area and X is the concentration in μg/20 μl.

B. Calculation Formulae

1. Chebulagic acid: The area of the peak appearing at $t_R$ 13.74 minutes is considered as Chebulagic acid and the amount calculated using the above mentioned calibration equation of Chebulinic acid (Y=209490383x+3958610) and the formula as follows. Chebulagic acid present in the extract (% w/w)=[Amount of chebulagic acid obtained using calibration equation (μg)/Amount of extract injected (μg)]×100.

2. Chebulinic acid: The area of the peak appearing at $t_R$ 20.66 minutes is considered as Chebulinic acid and the amount calculated using the above mentioned calibration equation of Chebulinic acid (Y=209490383x+3958610) and the formula as follows. Chebulinic acid present in the extract (% w/w)=[Amount of chebulinic acid obtained using calibration equation (μg)/Amount of extract injected (μg)]×100.

3. Other LMwHTs: The sum of the area of peaks appearing between 7-13 minutes, 15.681 minutes, 19.88, 23.107 minutes are added and the amount of other LMwHTs calculated using the calibration equation of Chebulinic acid (Y=209490383x+3958610) and the formula as follows. Other LMwHTs present in the extract (% w/w)=[Combined amount of Other LMwHTs obtained using calibration equation (μg)/Amount of extract injected (μg)]×100.

Herbal extracts can be made by grinding the herbs into a fine powder and suspending the powder into a solution of alcohol, water, and mixtures thereof. The suspension is regularly agitated or pulverized (e.g., by ultrasonication) over time and then pressed through a filtering medium to extract the bio-active ingredients.

In an embodiment, the extraction process of the current invention includes the steps of: providing fruits of T. chebula; pulverizing or grinding the T. chebula to a powder; extracting the T. chebula powder with an extraction solvent or solvent mixture, optionally, with heating, to provide a T. chebula enriched extract; and concentrating or drying the T. chebula enriched extract to provide a hydrolyzable tannoid enriched T. chebula powder. Aqueous solvent is preferred. A particularly preferred solvent is water. Useful extraction temperatures can range from about 25° C. (ambient) to about 90° C. Particularly useful extraction temperatures can range from about 25° C. to about 80° C.

Useful extraction times in conjunction with maintaining the useful temperatures can range from about 2 hours to about 16 hours. A particularly useful extraction time range at about 25° C. is from about 12 hours to about 16 hours. Length and temperature of extraction may be varied at atmospheric pressure (i.e., approx. 1 atm). It is contemplated that pressure can be varied in the extraction process, for example, by use of a commercial pressure reactor apparatus.

The extraction process can also include drying the extracted sample. Suitable drying methods include spray drying, lyophilization, freeze drying, vacuum drying (with or without heating), evaporation (with or without heating), and concentration under vacuum. Once isolated or obtained the hydrolyzable tannoid enriched T. chebula extract powder may be processed by any suitable means, including grinding, milling, sieving, sizing, and the like. The obtained hydrolyzable tannoid enriched T. chebula extract powder may be prepared in any suitable particle size or particle size range.

The nutraceutical compositions of the present invention may be administered in combination with a nutraceutically acceptable carrier. The active ingredients in such formulations may comprise from 1% by weight to 99% by weight, or alternatively, 0.1% by weight to 99.9% by weight. "Nutraceutically acceptable carrier" means any carrier, diluent or excipient that is compatible with the other ingredients of the formulation and not deleterious to the user. In accordance with one embodiment, suitable nutraceutically acceptable carriers can include ethanol, aqueous ethanol mixtures, water, fruit and/or vegetable juices, and combinations thereof. Similarly, the compositions as described may be used for pharmaceutical compositions, cosmetic compositions, or skin care compositions, and may be administered in combination with a pharmaceutically or cosmeceutically acceptable carrier, as appropriate.

Solid nutritional compositions for oral administration may optionally contain, in addition to the above enumerated nutritional composition ingredients or compounds: carrier materials such as corn starch, gelatin, acacia, microcrystalline cellulose, kaolin, dicalcium phosphate, calcium carbonate, sodium chloride, alginic acid, and the like; disintegrators including, microcrystalline cellulose, alginic acid, and the like; binders including acacia, methylcellulose, sodium carboxymethylcellulose, polyvinylpyrrolidone, hydroxypropyl methylcellulose, ethyl cellulose, and the like; and lubricants such as magnesium stearates, stearic acid, silicone fluid, talc, waxes, oils, colloidal silica, and the like. The usefulness of such excipients is well known in the art.

In a preferred embodiment, the nutritional composition may be in the form of a liquid. In accordance with this embodiment, a method of making a liquid composition is provided.

Liquid nutritional compositions for oral administration in connection with a method for preventing and/or treating free radical-induced illnesses or ailments, or various other inflammatory conditions or ailments, can be prepared in water or other aqueous vehicles. In addition to the above enumerated ingredients or compounds, liquid nutritional compositions can include suspending agents such as, for example, methylcellulose, alginates, tragacanth, pectin, kelgin, carrageenan, acacia, polyvinylpyrrolidone, polyvinyl alcohol, and the like. The liquid nutritional compositions can be in the form of a solution, emulsion, syrup, gel, or elixir including or containing, together with the above enumerated ingredients or compounds, wetting agents, sweeteners, and coloring and flavoring agents. Various liquid and powder nutritional compositions can be prepared by conventional methods. Various ready-to-drink formulations (RTD's) are contemplated.

The methods described above may be further understood in connection with the following Examples. The results of an extraction process depend upon the solvent used, temperature of extraction and duration of the extraction process. In several embodiment of this invention, these factors can be optimized to isolate and/or enrich and preserve the bioactives of T. chebula. T. chebula as used in the following examples was obtained from Ramakrishna Mission Ashrama, Narendrapur (Kolkata, West Bengal, India).

Example 1

Extraction of T. Chebula

In an embodiment, one optimized preparation of TC extract was prepared as follows. Fruit pericarp portions of T. chebula (50 g) were pulverized and the resulting powder was extracted with distilled water (300 ml) for 12 hours, with a continuous stirring (400 RPM), separately at 40±5° C. using a pressure reactor. Aliquots of the samples were withdrawn at different time intervals during extraction, spray dried and analyzed for bioactives (using standard methods as in examples above). As used herein, "0 hour" extraction refers to "instant extraction," which for the purpose of this disclosure means distilled water was added to the pulverized powder on a thermostatic water bath, stirred for 5 minutes and an aliquot of the sample withdrawn and analyzed.

Effect of duration of aqueous extraction at 40±5° C., on the bioactives content of T. chebula.

TABLE 1

| Bioactives | 0 Hr | 1 Hr | 2 Hr | 3 Hr | 4 Hr | 6 Hr | 8 Hr | 12 Hr |
|---|---|---|---|---|---|---|---|---|
| Chebulinic acid (% w/w) | 17.11 | 24.73 | 25.54 | 26.40 | 23.73 | 23.51 | 20.05 | 12.22 |
| Chebulagic acid (% w/w) | 8.15 | 15.68 | 15.20 | 16.93 | 14.04 | 15.52 | 14.93 | 12.90 |
| Other LMwHTs (% w/w) | 4.55 | 6.24 | 9.15 | 9.10 | 5.67 | 11.37 | 11.48 | 9.62 |
| Extractive value (% w/w) | 17.70 | 48.54 | 44.58 | 47.82 | 48.14 | 45.90 | 44.10 | 45.90 |

* indicates instant extraction

These findings suggest that for a composition having maximum chebulagic acid, chebulinic acid and LMwHTs, the optimum extraction conditions would be extraction at room temperature for 16 hours or extraction at 40±5° C. for about 3 hrs. However, it should be noted that the time of extraction may be substantially lowered by decreasing the particle size of the dried raw material, using stirring, performing the extraction process at higher pressures than the atmospheric pressure, altering the ratio of the fruit powder and the extraction solvent, and combinations of these parameters, or variation of other physical processing parameters.

Thus, the above extraction procedures yielded an enriched hydrolyzable tannoid blend. It is exemplary that other temperatures may be useful for all-aqueous extraction, such as, for example, 30° C., 40° C., 50° C., 60° C., 70° C., and 80° C. Useful extraction times may range from about 0 hours to about 24 hours. Other suitable extraction times may range from about 0 hours to about 6 hours, or from about 0 hours to about 4 hours, or from about 0 hours to about 3 hours, or from about 0 hours to about 2 hours.

Additionally, the above extraction procedures yielded total extractive tannin or tannoid compositions, that is, *T. chebula*/enriched tannoids of about 45% by weight, or greater, based on the total weight of the extract composition. In one embodiment, the total yield TC/enriched tannoids is about 50% by weight, or greater. In these embodiments, chebulinic acid and chebulagic acid can make up the greatest proportion of the total tannoids.

It is further expected that a hydrolyzable tannoid enriched *T. chebula* extract made in accordance with the principles of the invention would be effective as a nutritional supplement.

Example 2

Source of tested materials. *T. chebula* extracts were provided by Natreon, Inc., New Brunswick, N.J., USA.

Clinical Study. A randomized, double-blind, placebo-controlled, parallel group study to evaluate safety and analgesic efficacy of *Terminalia chebula* in subjects with Osteoarthritis of the knee.

Primary objective was to compare the efficacy of *Terminalia chebula* 250 mg BID and 500 mg BID with placebo in the treatment of osteoarthritis of the knee. The current study was planned to evaluate the analgesic property of *Terminalia chebula* 500 mg and 250 mg versus placebo, all given twice daily for twelve weeks using Modified WOMAC index scale (mWOMAC); pain relief as assessed by Visual analogue scale (VAS), and changes in Swelling index in subjects with osteoarthritis of the knee along with an assessment of the number of paracetamol tablets taken as rescue medication.

Secondary objective was to evaluate the safety and tolerability of *Terminalia chebula*.

Primary Outcome Measures: Modified Western Ontario and McMaster University OA Index (mWOMAC) is a disease specific outcome measure for osteoarthritis. It has three subscales assessing: pain—A (5 questions), stiffness-B (2 questions) and physical function-C (17 questions). The outcome was measured at baseline, week 4, week 8 and week 12. In this study the primary outcome was the reduction in modified WOMAC total score (A+B+C) from baseline to the end of treatment at week 12.

Secondary Outcome Measures:

1. VAS based assessment of Pain, Disability, and Stiffness subscales on the modified Western Ontario and McMaster University OA Index (mWOMAC). Pain Subscale is assessed by: no pain (0 mm) to extreme pain (100 mm). Stiffness Subscale is assessed by: no stiffness (0 mm) to extreme stiffness (100 mm). Disability (i.e., Physical Function) Subscale is assessed by: no disability (0 mm) to extreme disability (100 mm).

2. Swelling index as measured by joint circumference (in mm).

3. Use of rescue medication i.e., 650 mg paracetamol, in all treatment groups.

4. Physician global assessment, characterized by 5 categories: Excellent—complete relief of symptoms; Good—partial relief of symptoms; Fair—minimal relief of symptoms; Poor—no relief of symptoms; Very Poor—worsening of symptoms.

5. Tolerability was assessed by 3 categories. Good—no side effects; Fair—mild to moderate side effects; Poor—severe side effects and withdrawal of therapy.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

Study design. This was a randomized, double blind, parallel, placebo controlled study.

Subject Selection criteria. Inclusion criteria (S. no.): (1) Either gender, between the ages of 40 and 70 years. (2) Patients with Osteoarthritis of the knee of at least 6 months duration and meeting the ARA functional class I to III. (3) Radiological evidence of osteoarthritis. Only patients who have grade II to IV of the Kellgren and Lawrence scale will be recruited. (4) Subjects willing and able to discontinue all current analgesic therapy, including NSAIDs, OTC pain medications and topical analgesics. (5) Only those patients who record baseline pain scores of at least 40 mm on the VAS monitored at screening and baseline visits. (6) Ability to comply with the requirements of the study and to give informed consent and willing to come for regular follow up visits. Exclusion Criteria (S. no.): (1) Patients with severe osteoarthritis (ARA functional class IV). (2) Radiological grading—Kellgren and Lawrence scale ranging from grade 0 to grade I. (3) Patients on alternative system of medicine or physiotherapy. (4) Any psychiatric disorder or other conditions that might interfere with patients self assessment ability. (5) Systemic/Intraarticular steroids within 12 weeks and hyaluronic acid in the last 9 months, prior to baseline. (6) Arthroscopy within 1 year. (7) Candidates for imminent joint replacement. (8) Uncontrolled Hypertension or Diabetes; hepatic or renal impairment. (9) Pregnant or lactating females. (10) Participation within 30 days prior to screening in another investigational study. (11) Recent trauma of the involved knee.

Study medication (groups): *Terminalia chebula* (TC-500 mg)—1 capsule of 500 mg orally twice a day after food for a period of 12 weeks. *Terminalia chebula* (TC-250 mg)—1 capsule of 250 mg orally twice a day after food for a period of 12 weeks. Identical placebo capsule orally twice a day after food for a period of 12 weeks. Rescue medication: Paracetamol 650 mg. For comparison purposes, Crominex®3+(400 mcg dose; available from Natreon, Inc., New Brunswick, N.J.) or alternatively, a combination of TC-500 and Crominex®3+(400 mcg dose) were tested, orally administered.

Study Procedure.

Patients were enrolled in the present study after reading, understanding and signing the informed consent form. Then they were screened and assessed for the inclusion/exclusion criteria (visit 1). At the baseline/randomization visit (visit 2, study day 1), vital signs, general examination, routine lab investigations, modified WOMAC scoring, VAS for subjective assessment of pain, stiffness and disability respectively, swelling index for the involved joint were performed and all eligible subjects were randomized into the study medication to receive either one of the three treatments as per prior randomisation schedule. The study medication and rescue medication were dispensed at every visit and compliance checked by pill count method at every visit. Rescue medication accountability would be done to find out rescue medication consumption during the treatment period.

The subsequent 3 visits were scheduled at 4 weeks interval (visit 3—after 4 weeks of treatment, visit 4—after 8 weeks of treatment), vital signs, general examination, routine lab investigations, modified WOMAC scoring, VAS for subjective assessment of pain, stiffness and disability respectively, swelling index for the involved joint, and pill count for study and rescue medication were performed and each patient received another supply of the trial medication and rescue medication. At the conclusion of the study, visit 5 (after 12 weeks post treatment), vital signs, general examination, routine safety lab investigations, examination of the affected knee by modified WOMAC scoring, VAS for subjective assessment of pain, stiffness and disability respectively, and swelling index for the involved joint were performed. At every visit the patient was interviewed regarding any incidence of adverse effects (especially GI intolerance) and same noted in the case record form. Adverse Effects/Serious adverse event (SAE) monitoring is done throughout the course of study. Participant are given a contact number for reporting and accessing medical help with regard to any adverse event.

Statistical Analysis.

Primary and secondary end points were analyzed as the averaged change in the response over the 12-week treatment period. ANOVA and paired 't' test were used to compare the mean change from baseline to post treatment within group and unpaired "t" test for between group comparisons. All statistical analysis were performed using the Graph pad PRISM software 4 (Graph Pad Software Inc., San Diego, Calif., USA).

Study Results: A total of 22, 17 and 20 patients completed study in *T. chebula* 500 mg, *T. chebula* 250 mg and placebo groups, respectively. Baseline characteristics in all groups were similar suggesting homogenous population. As seen from the tables below, *Terminalia chebula* 500 mg twice daily produced significant improvement in signs and symptoms of osteoarthritis compared to baseline, *Terminalia chebula* 250 mg, and Placebo. The number of rescue medication (Paracetamol) tablets used was only 7±1.11 (SD) with *Terminalia chebula* 500 mg group, while it was 13±2.68 and 28±13.01 with *Terminalia chebula* 250 mg and placebo, respectively.

Safety assessments. All safety haematological, hepatic and renal biochemical parameters were within normal limits with all treatments. Gastrointestinal intolerance was the most commonly reported side effect in all treatment groups which was mild. Two subjects in the 500 mg group complained of dyspepsia and one had diarrhoea. In the Crominex 400 mcg group two subjects had diarrhoea, while two subjects in the combination group had dyspepsia and vomiting. None of the patients had any serious side effect and no subjects discontinued the study due to adverse events.

TABLE 2

DEMOGRAPHIC DATA

| | T chebula 500 mg, BID Group (A) | T chebula 500 mg BID + Crominex 400 mcg OD Group (B) | Crominex 400 mcg OD Group (C) | Placebo Group (D) | T chebula 250 mg, BID Group (E) |
|---|---|---|---|---|---|
| Total No. | 22 | 21 | 20 | 20 | 17 |
| Gender(M/F) | 9/13 | 10/11 | 13/7 | 12/8 | 9/8 |
| Age (yrs) | 59.18 ± 8.20 | 57.67 ± 8.11 | 55.9 ± 9.06 | 58.05 ± 6.07 | 58.35 ± 8.36 |
| Weight (Kg) | 75.51 ± 15.37 | 68.43 ± 14.88 | 61.63 ± 6.43 | 75.9 ± 8.24 | 75.41 ± 11.08 |
| BMI(Kg/m$^2$) | 29.54 ± 6.94 | 26.67 ± 5.29 | 26.14 ± 2.03 | 28.5 ± 3.73 | 27.47 ± 2.98 |

The detailed demographic characteristics of all the study groups are shown above in Table 2. There were no significant differences between treatment groups in baseline characteristics including age, weight and body mass index.

TABLE 3

Modified WOMAC score

| | T. chebula 500 mg, BID (A) | T. chebula 500 mg BID + Crominex 400 mcg OD (B) | Crominex 400 mcg OD (C) | Placebo (D) | T. chebula 250 mg BID (E) |
|---|---|---|---|---|---|
| BASELINE | 53.45 ± 7.42 | 53.00 ± 5.96 | 53.5 ± 5.89 | 51.95 ± 6.53 | 51.18 ± 7.45 |
| END OF 12 WEEKS | 33.64 ± 7.54* | 39.90 ± 9.86* | 44.7 ± 2.63* | 49.5 ± 6.13* | 40.71 ± 6.14* |
| ABSOLUTE CHANGE | 19.82 ± 8.35#* | 13.10 ± 5.69#*$^{NS}$ | 8.8 ± 4.61#*$^{NS}$ | 2.45 ± 3.07* | 10.47 ± 4.43*$^{NS}$ |

TABLE 3-continued

Modified WOMAC score

|  | T. chebula 500 mg, BID (A) | T. chebula 500 mg BID + Crominex 400 mcg OD (B) | Crominex 400 mcg OD (C) | Placebo (D) | T. chebula 250 mg BID (E) |
|---|---|---|---|---|---|
| % IMPROVEMENT IN MODIFIED WOMAC SCORE | 37.06 | 24.7 | 16.4 | 4.72 | 20.45 |

*P value < 0.001 compared to baseline in all the 5 groups
Absolute change in reduction of modified WOMAC scores:
AVs B, B Vs C (P < 0.01)
*A Vs D, A Vs C, A Vs E, B Vs D, C Vs D, C Vs E (P < 0.001)
[NS]B Vs E, C Vs E (P = NS)

As seen from Table 3, the baseline values of modified WOMAC score were comparable in all the 5 treatment groups. There was significant reduction in the modified WOMAC score after 12 weeks of treatment compared to baseline in all the 5 treatment groups (P value <0.001).

The % improvement in modified WOMAC score is in the following order: T. chebula 500 mg BID>T. chebula 500 mg BID+Crominex 400 mcg OD>T. chebula 250 mg BID>Crominex 400 mcg OD>Placebo.

TABLE 4

KNEE SWELLING INDEX (KSI)[1]

|  | T. chebula 500 mg, BID (A) | T.chebula 500 mg BID + Crominex 400 mcg OD (B) | Crominex 400 mcg OD (C) | Placebo (D) | T. chebula 250 mg BID (E) |
|---|---|---|---|---|---|
| BASELINE | 401.09 ± 43.93 | 366.19 ± 29.57 | 364.8 ± 21.30 | 404.1 ± 25.79 | 399.71 ± 37.26 |
| END OF 12 WEEKS | 372.14 ± 39.66* | 347.05 ± 32.59* | 349.1 ± 20.88* | 393.8 ± 25.45* | 381.47 ± 36.63* |
| ABSOLUTE CHANGE | 28.95 ± 16.82*@# | 19.14 ± 9.50*#@NS | 15.7 ± 7.59*#@ | 10.3 ± 3.8*@ | 18.24 ± 6.86#*Ns |
| % IMPROVEMENT IN MODIFIED WOMAC SCORE | 7.21 | 5.2 | 4.3 | 2.54 | 4.56 |

[1]Swelling index as measured by joint circumference (in mm).
*P value < 0.001, compared to baseline in all the 5 groups
Absolute change in reduction of Knee Swelling Index (KSI):
@A Vs B, C Vs D (P < 0.05)
A Vs E, B Vs C, C Vs E (P < 0.01)
*A Vs C, A Vs D, B Vs D, D Vs E (P < 0.001)
[NS]B Vs E (P = NS)

As seen from Table 4, the baseline values of KSI were comparable in all the 5 treatment groups. There was significant reduction in KSI after 12 weeks of treatment compared to baseline in all the 5 treatment groups (P value <0.001).

The percent reduction in KSI score is in the following order: T. chebula 500 mg BID>T. chebula 500 mg BID+Crominex 400 mcg OD>T. chebula 250 mg BID>Crominex 400 mcg OD>Placebo.

TABLE 5

VAS-PAIN SCORE

|  | T chebula 500 mg, BID (A) | T chebula 500 mg BID + Crominex 400 mcg OD (B) | Crominex 400 mcg OD (C) | Placebo (D) | T. chebula 250 mg BID (E) |
|---|---|---|---|---|---|
| BASELINE | 69.36 ± 5.69 | 72 ± 4.41 | 71 ± 4.59 | 66.4 ± 6.95 | 69.76 ± 6.74 |
| END OF 12 WEEKS | 44.95 ± 10.71* | 56.5 ± 5.64* | 61 ± 6.15* | 58.8 ± 7.30* | 57.06 ± 7.06* |

TABLE 5-continued

VAS-PAIN SCORE

|  | T chebula 500 mg, BID (A) | T chebula 500 mg BID + Crominex 400 mcg OD (B) | Crominex 400 mcg OD (C) | Placebo (D) | T. chebula 250 mg BID (E) |
|---|---|---|---|---|---|
| ABSOLUTE CHANGE | 24.41 ± 5.59* | 15.5 ± 5.36*@$^{NS}$ | 10 ± 5.27*@$^{NS}$ | 7.6 ± 9.24*$^{NS}$ | 12.71 ± 6.02*$^{NS}$ |
| % IMPROVEMENT IN MODIFIED WOMAC SCORE | 35.19 | 21.5 | 14.08 | 11.45 | 18.2 |

*P value < 0.001 compared to baseline in all the 5 groups
Absolute change in reduction of VAS-PAIN scores:
@B Vs C (P < 0.05)
*A Vs B, A Vs C, A Vs D, A Vs E, B Vs D (P < 0.001)
$^{NS}$C Vs D, B Vs E, C Vs E, D Vs E (P = NS)

As seen from Table 5, the baseline values of VAS-PAIN were comparable in all the 5 treatment groups. There was significant reduction in VAS-PAIN scores after 12 weeks of treatment compared to baseline in all the 5 treatment groups (P value <0.001).

The percent reduction in VAS-PAIN score is in the following order: T. chebula 500 mg BID>T. chebula 500 mg BID+Crominex 400 mcg OD>T. chebula 250 mg BID>Crominex 400 mcg OD>Placebo.

TABLE 6

VAS-STIFFNESS SCORE

|  | T. chebula 500 mg, BID (A) | T.chebula 500 mg BID + Crominex 400 mcg OD (B) | Crominex 400 mcg OD (C) | Placebo (D) | T. chebula 250 mg BID (E) |
|---|---|---|---|---|---|
| BASELINE | 63.59 ± 8.51 | 67.25 ± 3.02 | 65 ± 4.08 | 62.5 ± 3.69 | 62.41 ± 6.03 |
| END OF 12 WEEKS | 41.68 ± 12.10* | 53.75 ± 4.82* | 56.5 ± 6.26* | 51.7 ± 6.96* | 50.71 ± 7.20* |
| ABSOLUTE CHANGE | 21.91 ± 8.21* | 13.5 ± 4.62* $^{NS}$ | 8.5 ± 4.12*$^{NS}$ | 10.8 ± 6.36*$^{NS\#}$ | 11.71 ± 3.72*#$^{NS}$ |
| % IMPROVEMENT IN MODIFIED WOMAC SCORE | 34.46 | 20.07 | 13.08 | 17.28 | 18.76 |

*P value < 0.001 compared to baseline in all the 5 groups
Absolute change in reduction of VAS-STIFFNESS scores:
D Vs E (P < 0.05)
*A Vs B, A Vs C, A Vs D, A Vs E, B Vs D (P < 0.001)
$^{NS}$B Vs C, B Vs E, C Vs D, C Vs E (P = NS)

As seen from Table 6, the baseline values of VAS-STIFFNESS were comparable in all the 5 treatment groups. There was significant reduction in VAS-STIFFNESS scores after 12 weeks of treatment compared to baseline in all the 5 treatment groups (P value <0.001).

The percent reduction in VAS-STIFFNESS score is in the following order: T. chebula 500 mg BID>T. chebula 500 mg BID+Crominex 400 mcg OD>T. chebula 250 mg BID>Placebo>Crominex 400 mcg OD.

TABLE 7

VAS-DISABILITY SCORE

|  | T chebula 500 mg, BID (A) | T.chebula 500 mg BID + Crominex 400 mcg OD (B) | Crominex 400 mcg OD (C) | Placebo (D) | T. chebula 250 mg BID (E) |
|---|---|---|---|---|---|
| BASELINE | 57.95 ± 8.72 | 65.75 ± 5.45 | 61.5 ± 2.42 | 61.5 ± 4.39 | 56.59 ± 3.59 |
| END OF 12 WEEKS | 37.14 ± 13.27* | 52.5 ± 5.26* | 55 ± 4.08* | 53.1 ± 4.46* | 46.47 ± 5.81* |

TABLE 7-continued

VAS-DISABILITY SCORE

| | T chebula 500 mg, BID (A) | T.chebula 500 mg BID + Crominex 400 mcg OD (B) | Crominex 400 mcg OD (C) | Placebo (D) | T. chebula 250 mg BID (E) |
|---|---|---|---|---|---|
| ABSOLUTE CHANGE | 20.82 ± 8.46* | 13.25 ± 5.20*#$^{NS}$ | 6.8 ± 3.37*#$^{NS}$ | 8.4 ± 5.07*$^{NS@}$ | 10.12 ± 4.66*$^{@NS}$ |
| % IMPROVEMENT IN MODIFIED WOMAC SCORE | 35.92 | 20.15 | 11.0 | 13.66 | 17.88 |

*P value < 0.001 compared to baseline in all the 5 groups
Absolute change in reduction of VAS-DISABILITY scores:
@D Vs E (P < 0.05)
B Vs C (P < 0.01)
*A Vs B, A Vs C, A Vs D, A Vs E, B Vs D (P < 0.001)
$^{NS}$C Vs D, B Vs E, C Vs E (P = NS)

As seen from Table 7, the baseline values of VAS-DISABILITY were comparable in all the 5 treatment groups. There was significant reduction in VAS-DISABILITY score after 12 weeks of treatment compared to baseline in all the 5 treatment groups (P value <0.001).

The percent reduction in VAS-DISABILITY score is in the following order: T. chebula 500 mg BID>T. chebula 500 mg BID+Crominex 400 mcg OD>T. chebula 250 mg BID>Placebo>Crominex 400 mcg OD.

It can be concluded from the present study that treatment with T. chebula 500 mg BID, a combination of T. chebula 500 mg BID+Crominex 400 mcg OD, Crominex 400 mcg OD, and T. chebula 250 mg BID for a period of 12 weeks in osteoarthritis patients has shown a significant reduction in modified WOMAC score placebo, whereas T. chebula 500 mg BID, the combination of T. chebula 500 mg BID+Crominex 400 mcg OD both outperformed Crominex 400 mcg OD, T. chebula 250 mg BID and placebo. Both T. chebula and Crominex when given individually have shown reductions in the efficacy variables, but the predicted synergism of their combination was not observed. Further, T. chebula 500 mg BID group produced the best improvement in outcome parameters both statistically and clinically as compared to other treatment groups. The number of rescue medication tablets (Acetaminophen 650 mg) was minimally used by T. chebula 500 mg group as compared to other groups. The safety laboratory parameters were within normal limits at the end of study. All the study medications were well tolerated and no serious adverse events were observed and none of the patients have discontinued the study due to any adverse event. It was interesting to note that T. chebula (when administered at several doses) was devoid of significant GI side effects which are normally observed in patients routinely taking NSAIDs for symptomatic relief in OA.

Thus the T. Chebula compositions can be used to prepare anti-arthritic formulations that decrease pain and inflammation.

The nutraceutical compositions of the T. chebula extracts may be administered in combination with a nutraceutically acceptable carrier. The active ingredients in such formulations may comprise from 1% by weight to 99% by weight, or alternatively, 0.1% by weight to 99.9% by weight. "Nutraceutically acceptable carrier" means any carrier, diluent or excipient that is compatible with the other ingredients of the formulation and not deleterious to the user. In accordance with one embodiment, suitable nutraceutically acceptable carriers can include ethanol, aqueous ethanol mixtures, water, fruit and/or vegetable juices, and combinations thereof. Similarly, the compositions as described may be used for pharmaceutical compositions, cosmetic compositions, or skin care compositions, and may be administered in combination with a pharmaceutically or cosmeceutically acceptable carrier, as appropriate.

The pharmaceutical compositions of the T. chebula extracts may be administered in combination with a pharmaceutically acceptable carrier. The active ingredients in such formulations may comprise from 1% by weight to 99% by weight, or alternatively, 0.1% by weight to 99.9% by weight. "Pharmaceutically acceptable carrier" means any carrier, diluent or excipient that is compatible with the other ingredients of the formulation and not deleterious to the user.

Solid nutritional compositions for oral administration may optionally contain, in addition to the above enumerated nutritional composition ingredients or compounds: carrier materials such as, but not limited to, corn starch, gelatin, acacia, microcrystalline cellulose, kaolin, dicalcium phosphate, calcium carbonate, sodium chloride, alginic acid, and the like; disintegrators including, microcrystalline cellulose, alginic acid, and the like; binders including acacia, methylcellulose, sodium carboxymethylcellulose, polyvinylpyrrolidone, hydroxypropyl methylcellulose, ethyl cellulose, and the like; and lubricants such as magnesium stearates, stearic acid, silicone fluid, talc, waxes, oils, colloidal silica, and the like. The usefulness of such excipients is well known in the art.

In one embodiment, the nutritional composition may be in the form of a liquid. In accordance with this embodiment, a method of making a liquid composition is provided.

Liquid nutritional compositions for oral administration in connection with a method for preventing and/or treating arthritis, or inflammatory symptoms thereof, can be prepared in water or other aqueous vehicles. In addition to the above enumerated ingredients or compounds, liquid nutritional compositions can include suspending agents such as, for example, methylcellulose, alginates, tragacanth, pectin, kelgin, carrageenan, acacia, polyvinylpyrrolidone, polyvinyl alcohol, and the like. The liquid nutritional compositions can be in the form of a solution, emulsion, syrup, gel, or elixir including or containing, together with the above enumerated ingredients or compounds, wetting agents, sweeteners, and coloring and flavoring agents. Various liquid and powder nutritional compositions can be prepared by conventional methods. Various ready-to-drink formulations (RTD's) are contemplated.

Delivery System

Suitable dosage forms include tablets, capsules, solutions, suspensions, powders, gums, and confectionaries. Sublingual delivery systems include, but are not limited to, dissolvable tabs under and on the tongue, liquid drops, and beverages. Edible films, hydrophilic polymers, oral dissolvable films or oral dissolvable strips can be used. Other useful delivery systems comprise oral or nasal sprays or inhalers, and the like.

For oral administration, *T. chebula* extracts may be further combined with one or more solid inactive ingredients for the preparation of tablets, capsules, pills, powders, granules or other suitable dosage forms. For example, the active agent may be combined with at least one excipient such as fillers, binders, humectants, disintegrating agents, solution retarders, absorption accelerators, wetting agents, absorbents, or lubricating agents. Other useful excipients include magnesium stearate, calcium stearate, mannitol, xylitol, sweeteners, starch, carboxymethylcellulose, microcrystalline cellulose, silica, gelatin, silicon dioxide, and the like.

The components of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof many comprise conventional ingredients in conventional proportions, with or without additional active compounds or principles, and such unit dosage forms may contain any suitable effective amount of the active ingredient commensurate with the intended daily dosage range to be employed.

The components of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid, which is in a mixture with the finely divided active component. In tablets, the active component is mixed with the carrier having the necessary binding capacity in suitable proportions and compacted in the shape and size desired.

The powders and tablets preferably contain from five or ten to about seventy percent of the active compound(s). Suitable carriers are magnesium carbonate, magnesium state, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges are included. Tablets, powders, capsules, pills, cachets, and lozenges can be used as solid forms suitable for oral administration.

Liquid preparations include solutions, suspensions, and emulsions, for example, water or water-propylene glycol solutions. For example, parenteral injection liquid preparations can be formulated as solutions in aqueous polyethylene glycol solution. The chemical compound according to the present invention may thus be formulated for parenteral administration (e.g. by injection, for example bolus injection or continuous infusion) and may be presented in unit dose for in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavors, stabilizing and thickening agents, as desired. Aqueous suspensions suitable for oral use can be made by dispersing the finely divided active component in water with viscous material, such as natural or synthetic gums, resins, methylcellulose, sodium carboxymethylcellulose, or other well known suspending agents.

Compositions suitable for topical administration in the mouth includes lozenges comprising the active agent in a flavored base, usually sucrose and acacia or tragacanth; pastilles comprising the active ingredient in an inert base such as gelatin and glycerine or sucrose and acacia; and mouthwashes comprising the active ingredient in suitable liquid carrier.

Solutions or suspensions are applied directly to the nasal cavity by conventional means, for example with a dropper, pipette or spray. The compositions may be provided in single or multi-dose form. In compositions intended for administration to the respiratory tract, including intranasal compositions, the compound will generally have a small particle size for example of the order of 5 microns or less. Such a particle size may be obtained by means known in the art, for example by micronization.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenges itself, or it can be the appropriate number of any of these in packaged form.

Tablets, capsules and lozenges for oral administration and liquids for oral use are preferred compositions. Solutions or suspensions for application to the nasal cavity or to the respiratory tract are preferred compositions. Transdermal patches for topical administration to the epidermis are preferred.

Further details on techniques for formulation and administration may be found in the latest edition of Remington's Pharmaceutical Sciences (Mack Publishing Co., Easton, Pa.).

Solid nutritional compositions for oral administration may optionally contain, in addition to the above enumerated nutritional composition ingredients or compounds: carrier materials such as corn starch, gelatin, acacia, microcrystalline cellulose, kaolin, dicalcium phosphate, calcium carbonate, sodium chloride, alginic acid, and the like; disintegrators including, microcrystalline cellulose, alginic acid, and the like; binders including acacia, methylcellulose, sodium carboxymethylcellulose, polyvinylpyrrolidone, hydroxypropyl methylcellulose, ethyl cellulose, and the like; and lubricants such as magnesium stearate, stearic acid, silicone fluid, talc, waxes, oils, colloidal silica, and the like. The usefulness of such excipients is well known in the art.

In one preferred embodiment, the nutritional composition may be in the form of a liquid. In accordance with this embodiment, a method of making a liquid composition is provided.

Liquid nutritional compositions for oral administration in connection with a method for preventing and/or treating inflammation, colds and/or flu can be prepared in water or other aqueous vehicles. In addition to the above enumerated ingredients or compounds, liquid nutritional compositions can include suspending agents such as, for example, methylcellulose, alginates, tragacanth, pectin, kelgin, carrageenan, acacia, polyvinylpyrrolidone, polyvinyl alcohol, and the like. The liquid nutritional compositions can be in the form of a solution, emulsion, syrup, gel, or elixir including or containing, together with the above enumerated ingredients or compounds, wetting agents, sweeteners, and coloring and flavoring agents. Various liquid and powder nutritional compositions can be prepared by conventional methods. Various ready-to-drink formulations (RTD's) are contemplated.

Routes of Administration

The compositions may be administered by any suitable route, including but not limited to oral, sublingual, buccal, ocular, pulmonary, rectal, and parenteral administration, or as an oral or nasal spray (e.g. inhalation of nebulized vapors, droplets, or solid particles). Parenteral administration includes, for example, intravenous, intramuscular, intraarterial, intraperitoneal, intranasal, intravaginal, intravesical (e.g., to the bladder), intradermal, transdermal, topical, or subcutaneous administration. Also contemplated within the scope of the invention is the instillation of a pharmaceutical composition in the body of the patient in a controlled formulation, with systemic or local release of the drug to occur at a later time. For example, the drug may be localized in a depot for controlled release to the circulation, or for release to a local site.

Pharmaceutical compositions of the invention may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflations, including powders and liquid aerosol administration, or by sustained release systems. Suitable examples of sustained release systems include semipermeable matrices of solid hydrophobic polymers containing the compound of the invention, which matrices may be in form of shaped artices, e.g. films or microcapsules.

The use of the terms "a," "an," "the," and similar referents in the context of describing the presently claimed invention (especially in the context of the claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Use of the term "about" is intended to describe values either above or below the stated value in a range of approx. ±10%; in other embodiments the values may range in value either above or below the stated value in a range of approx. ±5%; in other embodiments the values may range in value either above or below the stated value in a range of approx. ±2%; in other embodiments the values may range in value either above or below the stated value in a range of approx. ±1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

I claim:

1. A method of treating osteoarthritis in a mammal, comprising administering to a mammal in need thereof a therapeutically effective amount of a a composition comprising a *Terminalia chebula* extract comprising a hydrolyzable tannoid blend, said blend comprising about 8-25% by weight chebulagic acid based on the total weight of the extract and about 15-30% by weight chebulinic acid based on the total weight of the extract.

2. The method of claim 1, wherein the composition is administered in a dosage from about 100 mg per day to about 5000 mg per day.

3. The method of claim 1, wherein the composition is administered in a dosage from about 500 mg per day to about 1000 mg per day.

4. The method of claim 1, wherein the mammal is selected from the group consisting of human, dog, cat, cow, horse, monkey, pig, sheep, cow, sheep, goat, and rabbit.

5. The method of claim 2, wherein the mammal is a human.

6. The method of claim 3, wherein the mammal is a human.

7. A method of reducing pain and inflammation in an individual with osteoarthritis in need thereof, comprising orally administering to the individual in need thereof a therapeutically effective amount of a a composition comprising a *Terminalia chebula* extract comprising a hydrolyzable tannoid blend, said blend comprising about 8-25% by weight chebulagic acid based on the total weight of the extract and about 15-30% by weight chebulinic acid based on the total weight of the extract.

8. The method of claim 7, wherein the composition is administered in a dosage from about 100 mg per day to about 5000 mg per day.

9. The method of claim 7, wherein the composition is administered in a dosage from about 500 mg per day to about 1000 mg per day.

10. The method of claim 7, wherein the individual is treated for about 2 weeks to about 12 weeks.

11. The method of claim 10, wherein pain and inflammation in the individual is measured by a modified Western Ontario and McMaster Universities Osteoarthritis (mWOMAC) scale to provide an index score, wherein the mWOMAC index score is reduced by about 20% to about 40%.

12. The method of claim 10, wherein pain and inflammation in the individual is measured by one of more subscales of Visual Analogue Scale (VAS), wherein the subscales are VAS-Pain, VAS-Stiffness, or VAS-Disability subscales and wherein the one or more subscales provide a score, and wherein the score is reduced by about 20% to about 40%.

13. The method of claim 10, further comprising measuring knee swelling index, wherein the knee swelling index is reduced by about 5% to about 10%.

* * * * *